United States Patent
Vogler

(10) Patent No.: US 8,425,496 B2
(45) Date of Patent: Apr. 23, 2013

(54) OPTICAL IMAGING SYSTEM, PARTICULARLY IN A LASER SURGICAL OPHTHALMIC APPARATUS

(75) Inventor: Klaus Vogler, Eckental/Eschenau (DE)

(73) Assignee: Wavelight AG, Erlangen (DE)

( * ) Notice: Subject to any disclaimer, the term of this patent is extended or adjusted under 35 U.S.C. 154(b) by 969 days.

(21) Appl. No.: 12/420,999

(22) Filed: Apr. 9, 2009

(65) Prior Publication Data

US 2010/0262128 A1  Oct. 14, 2010

(51) Int. Cl.
*A61F 9/008* (2006.01)

(52) U.S. Cl.
USPC .................................. 606/4; 606/9

(58) Field of Classification Search ............. 606/4–6; 351/221
See application file for complete search history.

(56) References Cited

U.S. PATENT DOCUMENTS

| | | | |
|---|---|---|---|
| 6,512,781 B1 * | 1/2003 | Borstel et al. ............. | 372/19 |
| 6,905,641 B2 * | 6/2005 | Platt et al. ............... | 264/1.38 |
| 2004/0263959 A1 * | 12/2004 | Dixon et al. ............. | 359/385 |
| 2008/0186551 A1 | 8/2008 | Hanft et al. | |
| 2008/0259425 A1 | 10/2008 | Boettcher | |
| 2010/0286674 A1 * | 11/2010 | Ben-Yakar et al. ........ | 606/10 |
| 2011/0178512 A1 * | 7/2011 | Blumenkranz et al. ...... | 606/6 |

FOREIGN PATENT DOCUMENTS

| | | |
|---|---|---|
| DE | 4424492 | 1/1996 |
| DE | 102005013949 A1 | 9/2006 |
| EP | 0326760 | 8/1989 |
| WO | WO-01/15592 | 3/2001 |
| WO | 03032803 A2 | 4/2003 |

OTHER PUBLICATIONS

Menn, Steven, et al., "Spieglein, Spieglein . . . ," Laser and Photonic, Apr. 2007, pp. 18-22.
European Patent Office, International Search Report dated Dec. 14, 2009, Application No. PCT/EP2009/002659, 16 pages.

* cited by examiner

*Primary Examiner* — Bill Thomson
*Assistant Examiner* — Jeffrey Lipitz
(74) *Attorney, Agent, or Firm* — Haynes and Boone, LLP

(57) ABSTRACT

An optical imaging system comprises at least one deformable mirror (34) and an adjustment and control arrangement (36, 38) which is coupled to the mirror and is adapted to displace the image-side focal point (52) of the imaging system in the beam propagation direction by deformation of the mirror, particularly in accordance with a predetermined focal point displacement profile. The optical imaging system is preferably employed in a device for femtosecond laser surgery of the human eye, for example for corneal lenticle extraction.

7 Claims, 4 Drawing Sheets

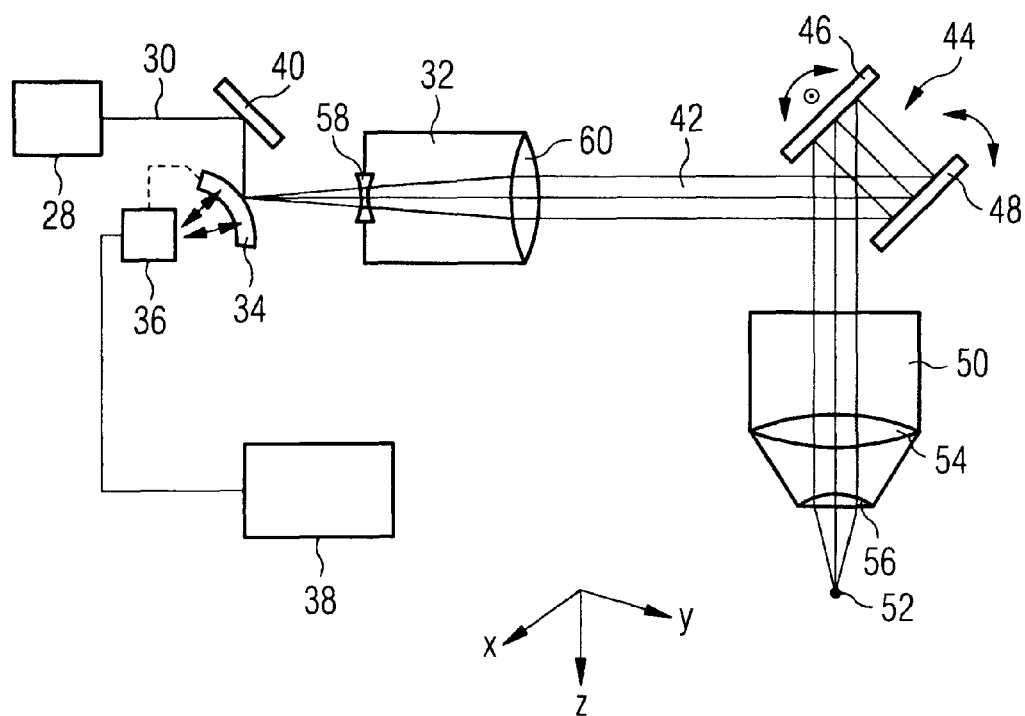

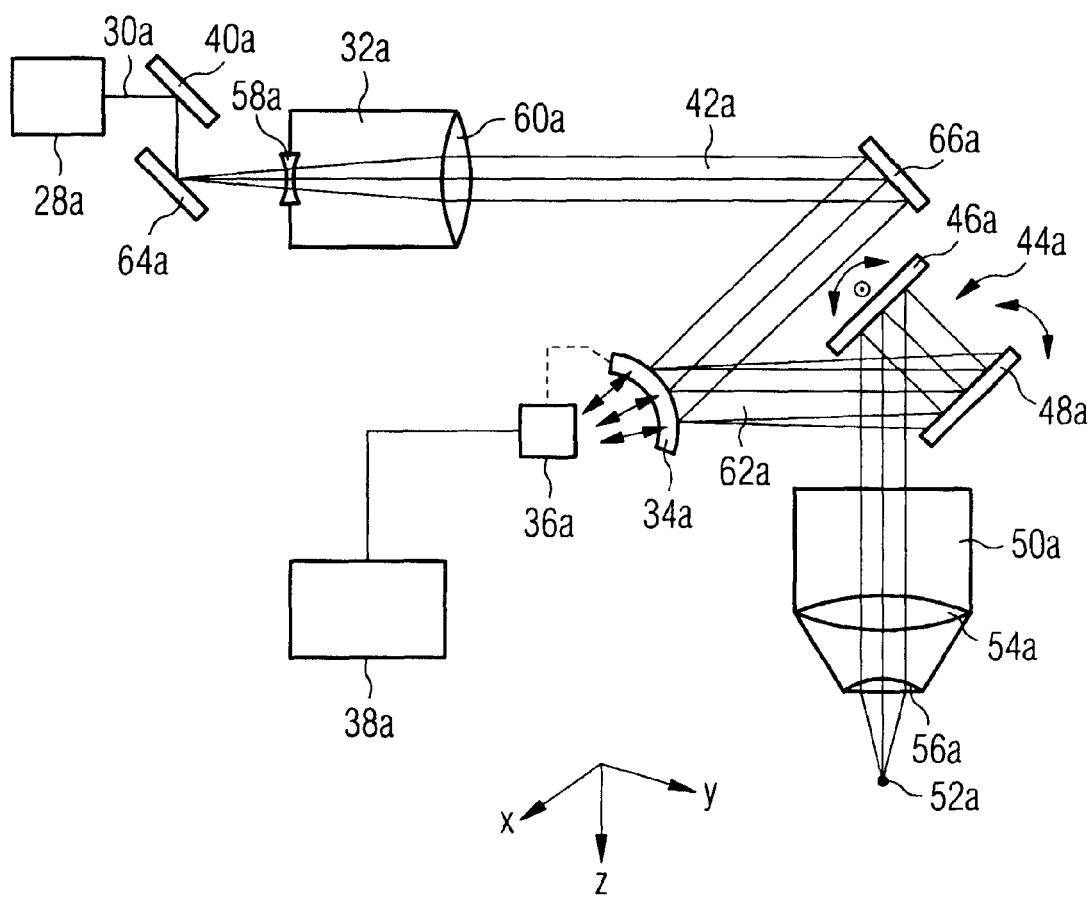

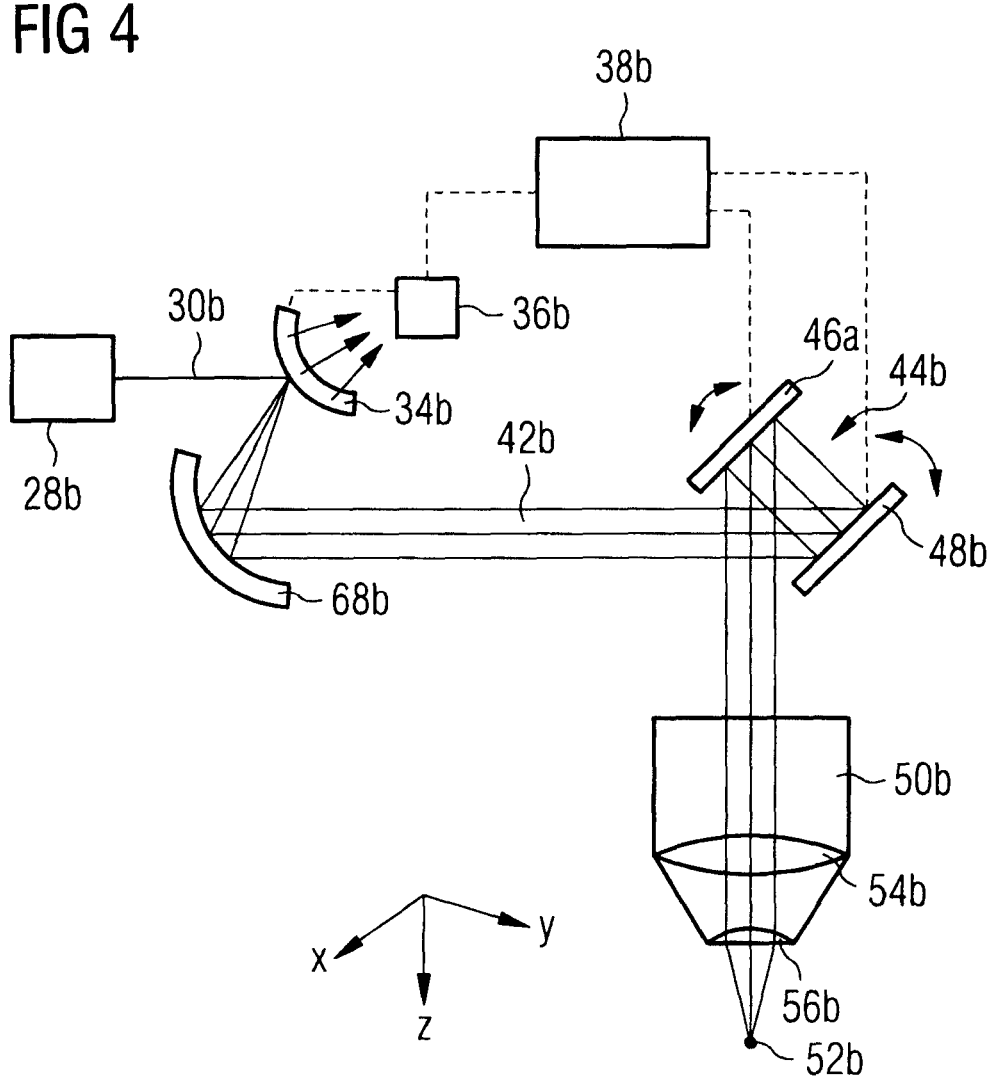

OPTICAL IMAGING SYSTEM, PARTICULARLY IN A LASER SURGICAL OPHTHALMIC APPARATUS

Figure 1:
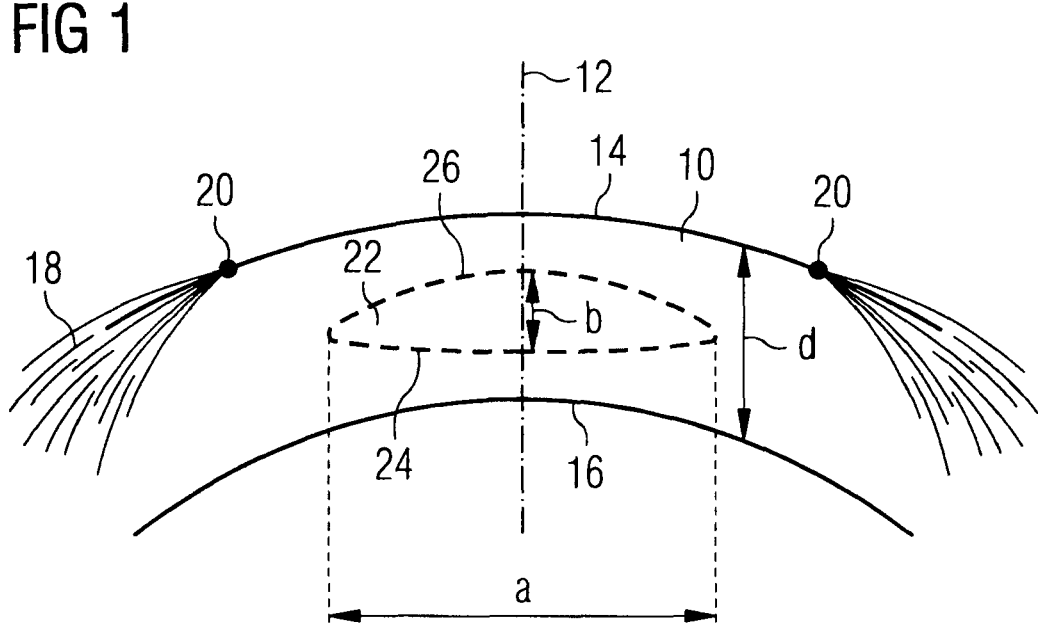

The invention relates to an optical imaging system which may be used particularly in a device for laser surgical opthalmology, but also in laser systems for other processing tasks, for example in photovoltaics or in industrial material processing.

In particular, the invention provides an optical imaging system which allows the focus of a laser beam sent through the imaging system to be displaced rapidly in the z direction, the z direction according to conventional nomenclature denoting the direction of the beam path (beam propagation direction). An x or y direction is then to be understood as any direction in a plane orthogonal to the z direction. In this plane, movement of the laser beam is conventionally carried out by means of a scanner for the purpose of scanning a material region to be processed by means of the laser beam; the material to be processed may be living or dead material.

Laser systems, which emit short-pulse radiation in the femtosecond range, are used in eye surgery inter alia to make intratissue incisions in the cornea, but also in the human lens. The effect employed in this case is optical break-through, which leads to so-called photodisruption of the exposed tissue. The generation of such photodisruptions requires comparatively strong focusing of the laser beam, which is achieved by a correspondingly large aperture of the focusing optics used for the focusing. In known opthalmological fs laser systems, the focusing optics are usually formed by a so-called f-theta objective which ensures plane field imaging and avoids undesired displacements of the beam focus in the z direction when scanning the laser beam.

Fs laser systems have an important place in opthalmology, for example for LASIK applications. LASIK stands for laser in situ keratomileusis, and refers to a corneal treatment technique for correcting visual defects in which a so-called "flap", still partially connected to the corneal tissue, is cut out on the corneal surface, this flap is then folded to the side and the stromal tissue exposed after folding the flap away is ablated with short-wave laser light, for example an excimer laser emitting at 193 nm, in accordance with a patient-specifically determined ablation profile.

In order to produce the flap cut, it is known to flatten the eye to be treated by means of an applanation plate and to guide the beam focus two-dimensionally in a plane inside the cornea. Owing to the plane field imaging provided by the f-theta objective, this does not require any z displacement of the focus. Displacement of the focal positions in the z direction may be necessary only in the edge region of the flap, if the marginal cut of the flap is intended to be taken upwards from the stroma.

Various solutions have been proposed in the prior art for focal displacement in the z direction. WO 03/032803 A2 proposes to displace the focusing objective as a whole in the direction of the z axis, i.e. along the beam path. A variant of this would be to configure the focusing objective as a zoom objective. However, both methods have the disadvantage that the mechanical displacement or zoom setting of the focusing objective must be carried out very precisely, since this is transformed into a 1:1 adjustment of the focal position. For a focal displacement by a few μm desired between successive pulses of the laser beam, correspondingly rapid mechanical displacement of the focusing objective or a zoom lens of the objective would therefore be required over the same distance. Conventional mechanical drives are not suitable for this.

An alternative solution is presented in DE 10 2005 013 949 A1. The laser system therein has two-lens expansion optics (beam expander) designed as a telescope, a downstream scanner and, after the scanner, a focusing lens. The expansion optics' entry lens, configured as a concave lens, can be displaced in the beam direction, i.e. in the z direction, by means of a linear drive. Such displacement of the entry lens modifies the divergence of the laser beam emerging from the expansion optics. If the position of the focusing lens (f-theta objective) remains constant, the focal position is therefore moved in the z direction.

An advantage of this solution over z displacement of the focusing optics resides in the better reproducibility and higher displacement accuracy, because the optical imaging system transforms the displacement movement of the entry lens of the beam expander down to a displacement movement of the focal position which is reduced, for example, by a factor of 10. However, the adjustment rate achievable for the entry lens places limits on the beam focus' displacement rate transformed into the focal plane. For a three-dimensional cut, as is required for example for a corneal lenticle extraction, the focal adjustment method according to DE 10 2005 013 949 A1 is admittedly much faster than the method presented in WO 03/032803 A2, simply because the masses to be moved in the case of adjusting the entry lens of the beam expander are much less than in the case of adjusting the entire focusing optics. Contemporary focusing optics may readily weigh several kilograms, but must still be movable without vibrations. The entry lens of the beam expander, on the other hand, can have a comparatively small aperture and correspondingly be small and light-weight. Nevertheless, conventional linear drives do not satisfy the requirements when an intracorneal lenticle cut or another three-dimensional incision is intended to be made in an acceptably short time with a laser which repeats sufficiently fast. The adjustment rates possible for reliable, tilt-free guidance of the entry lens of the beam expander are for example between about 1 and 3 mm/s with conventional linear drives, although up to about 5 mm/s may also be achievable with tolerable outlay for the mechanical guidance of the entry lens. However, for a lenticle cut when using an fs laser which repeats in the two- to three-figure kHz range or even faster, with the same principle of z focus adjustment, entry lens adjustment rates of at least 10 mm/s or more would be necessary, which cannot be achieved with commercially available linear drive systems, at least not with those systems which satisfy the requirements for the adjustment accuracy and the guidance precision.

As an alternative to linear displaceability of the entry lens of the beam expander, DE 10 2005 013 949 A1 proposes to place two concave mirrors in the beam path between the laser and the scanner, the divergence of the laser beam and therefore its focal position in the z direction being variable by changing the mutual spacing of the concave mirrors. Here again, comparable limitations exist for the speed of the mechanical adjustment.

It is an object of the invention to provide an optical imaging system which is more suitable for three-dimensional focal guidance in material processing, and particularly in opthalmology.

In order to achieve this object, the invention provides an optical imaging system having at least one deformable mirror and an adjustment and control arrangement, which is coupled to the mirror and is adapted to displace the image-side focal point of the imaging system in the beam propagation direction by deformation of the mirror, particularly in accordance with a predetermined focal point displacement profile.

Deformable mirrors and their use in laser systems are known per se. For example, in this regard reference may be made to S. Menn, P. Bierden, "Spieglein, Spieglein . . . , Technologische Fortschitte and Anwendungen verformbarer Mikrospiegel" [Mirror, Mirror . . . , technological progress and applications of deformable micromirrors] in Laser+Photonik 4/2007, pages 18-22. In particular, according to the information in this article deformable mirrors can be divided into five different basic variants, namely deformable MEMS mirrors (MEMS: micro-electromechanical system), piezoelectric deformable mirrors, deformable membrane mirrors, bimorphic deformable mirrors and ferromagnetic deformable mirrors. The invention is not intended to be restricted to particular instances of these various mirror types. In principle, it is possible to use any deformable mirrors which allow a desired modification of the wavefront of an incident laser beam in the scope of laser systems. By using deformable (adaptive) mirrors in the beam guidance of an fs laser, much faster z displacement of the beam focus can be achieved in comparison with conventional mechanical linear adjustment systems, for example approximately an order of magnitude faster.

One known application field of adaptive mirrors is for example in astronomical observation. There, perturbed wavefronts are converted by means of adaptive mirrors into plane wavefronts so as to improve the image quality of the received light distorted by atmospheric interference. In contrast to this, the invention does not attempt to eliminate undesired wavefront perturbations by corresponding deformation of a deformable mirror. Instead, by suitable adjustment of a deformable mirror, the invention aims to deform the wavefront of a light beam incident on the mirror so that the image-side focal point of the imaging system and therefore the beam focus are displaced in a desired way in the z direction. Preferably, the adjustment and control arrangement is adapted to adjust the mirror to a shape such that an essentially plane incident wave is converted into a reflected wave with an essentially uniformly curved wavefront, the strength of the wavefront curvature depending on the desired position of the focal point in the beam propagation direction. The uniformity of the wavefront curvature is desirable for a high beam quality at the focus. The invention therefore essentially reverses the conventional use of adaptive mirrors for improving the planarity of the wavefront, and deliberately generates a defined, constantly variable wavefront curvature from an approximately plane wavefront. The wavefront curvature generated may imply an increase or decrease in divergence, so that the beam focus is displaced in one direction or the other starting from a predetermined neutral position.

In one embodiment, the mirror may be arranged before a telescope in the beam propagation direction. In another embodiment, on the other hand, it may be arranged after a telescope in the beam propagation direction but before focusing optics having at least a single lens, and preferably before a scanner. According to yet another embodiment, it is furthermore conceivable to construct beam expansion optics from two mirrors and to configure one of the mirrors as an adaptive deformable mirror, by means of which a desired divergence can be introduced into the beam.

The rapid focal displacement in the z direction, facilitated by the invention, is particularly attractive for use in those opthalmological applications which operate with fast-repeating focused fs laser radiation and require rapid three-dimensional incision guidance for short treatment times. Accordingly, another aspect of the invention provides a device for laser surgical opthalmology, having a source of a pulsed femtosecond laser beam, beam expansion optics which expand the laser beam, a scanner downstream of the beam expansion optics for deflecting the laser beam in a plane perpendicular to the beam path, and focusing optics downstream of the scanner, for focusing the laser beam, wherein the device has a deformable mirror arranged between the laser source and the focusing optics in the beam propagation direction, and a program-controlled adjustment and control arrangement which is coupled to the mirror and is adapted to deform the mirror for displacement of the beam focus in the direction of the beam path in accordance with a predetermined cutting profile to be produced in a patient's eye and represented by a control program. The adjustment and control arrangement may be adapted to control the mirror so that the beam focus of the laser beam can be displaced by at least 100 µm, preferably at least 150 µm, more preferably at least 200 µm in the direction of the beam path, and specifically just by corresponding control of the deformable mirror without adjustment of the focusing optics or other components of the optical imaging system.

One possible application which may profit from the rapid three-dimensional incision guidance of the invention is corneal lenticle extraction, in which an approximately lens-shaped volume element is cut out from the stroma of the cornea in order to correct the refraction of the cornea. Precise and rapid three-dimensional positioning of the foci of the fs laser pulses is important for this. In the x-y direction, this is not a problem with correspondingly fast operation of the scanner. For example, conventional mirror scanners which operate according to the galvanometer principle are readily capable of ensuring the required deflections even with pulse repetitions in the MHz range. In the z direction, an excursion of the beam focus in the high two-figure to three-figure µm range is readily possible within a few milliseconds or at least a few tens of milliseconds by using a deformable mirror. For a corneal lenticle extraction, for example, this allows the entire lenticle cut to be made in a few minutes (for example 2-4 minutes) or even in less than 1 minute, depending on the size of the lenticle, which limits the discomfort experienced by the patient in such an operation to a time which is as short as possible. Furthermore, the invention opens up the opportunity for refractive correction of the eye without the previously conventional use of an excimer laser since, during the lenticle extraction, the high precision and reproducibility of the z positioning of the beam focus allow beam guidance which is accurately matched to the visual defects to be corrected.

The invention will be described in more detail below with the aid of the appended drawing, in which:

FIG. 1 schematically shows in section a part of the human eye comprising the cornea, with the corneal lenticle cut indicated, FIG. 2 schematically shows an example of a device according to the invention for laser surgical opthalmology, FIG. 3 shows a first variant of such a laser surgical opthalmological device, and FIG. 4 shows another variant.

Reference will first be made to FIG. 1. This shows the cornea, denoted by 10, of a human eye in a sectional representation. The optical axis (vision axis) of the eye is indicated by dots and dashes and denoted by 12. The cornea 10 has an anterior surface 14 and a posterior surface 16. Its thickness d for a typical human eye lies in the range of around 500 µm, although variations up or down are of course possible from person to person. The sclera and the limbus of the eye are indicated by 18 in FIG. 1, and the limbus edge is denoted by 20.

Also indicated by dashes in FIG. 1 is an intracorneal, or more precisely intrastromal lenticle 22 to be cut out by treatment with focused fs laser radiation, which is subsequently extracted operatively through an opening to be introduced laterally into the cornea 10. This opening may also be produced by a laser cut. Femtosecond lenticle extraction allows correction of visual defects, for example myopia and myopic astigmatism. The lenticle 22 is conventionally produced by an essentially flat rear cut 24 and a curved front cut 26. The lenticle diameter—denoted by a in FIG. 1—lies for example in the range of between about 6 and 8 mm, while the typical lenticle thickness denoted by b is for example about 80-100 µm. With these values for the lenticle thickness, visual defects of about −5 dpt to −6 dpt can be corrected. It is to be understood that both the lenticle diameter and the lenticle thickness may vary according to the strength of the visual defect to be corrected. In any event, however, the lenticle thickness will regularly be a few tens of µm, which in conjunction with an approximately flat lenticle lower side (defined by the rear lenticle cut 24) means that in a line scan of a laser beam over the lenticle apex (i.e. were the lenticle 22 has the greatest thickness) the beam focus of the laser beam must execute an excursion corresponding to the lenticle thickness in the beam propagation direction.

Reference will now also be made to FIG. 2. The laser device shown therein comprises a femtosecond laser source 28, formed for example by a fibre laser, which generates pulsed laser radiation 30 with pulse durations in the femtosecond range and a pulse repetition rate which preferably lies in the high two-figure to three-figure kHz range, or even in the MHz range. The generated laser beam is expanded by expansion optics 32. Before the expansion optics 32 in the beam propagation direction, there is an active deformable mirror 34 whose deformation state can be adjusted by an actuator arrangement generally denoted by 36, which is in turn driven by a program-controlled control unit 38. The mirror 34 has a multiplicity of individual mirror facets adjustable by means of the actuator arrangement 36, and the actuator arrangement 36 may for example have piezo actuation elements, MEMS actuation elements, DMD actuation elements (DMD: digital micromirror device) or LCD actuation elements (LCD: liquid-crystal device).

The mirror 34 is furthermore preceded in the exemplary case shown by a passive deviating mirror 40, which however has no effect or at least no substantial effect on the wavefront characteristic and therefore the divergence of the laser beam 30.

The laser beam expanded by the expansion optics—and denoted by 42—subsequently travels to a scanner 44, the purpose of which is to deflect the laser beam 42 in an x-y plane orthogonal to the beam propagation direction (z direction; cf. the coordinate system likewise indicated in FIG. 2) and thereby to scan the laser beam over the eye's region to be treated. In the exemplary case shown, the scanner functions according to the galvanometer principle and is formed by two tiltable deflecting mirrors 46, 48 drivable by the control unit 38. It is to be understood that scanners operating according to other principles (for example scanning by means of a suitably controllable crystal) are equally possible.

The scanner 44 is followed by a focusing objective 50, in particular an f-theta objective, which focus the laser beam onto a focal position 52. In the exemplary case shown, the focusing objective 50 is configured with two lenses 54, 56. It is to be understood that the objective 50 may readily be configured with any other desired number of lenses. The embodiment of the focusing objective as an f-theta objective leads to plane field imaging, for which the focal position 50 always lies in a plane orthogonal to the z direction irrespective of the deflection angle of the laser beam.

In the exemplary case shown, the beam expansion optics 32 are formed by a Galilean telescope having an entry lens 58 with negative refracting power (concave lens) and an exit lens 60 with positive refracting power (converging lens). As an alternative, a Keppler version of the telescope with two convex lenses is possible.

The laser beam 30 incident on the mirror 34 has an essentially plane wavefront, which, according to one exemplary embodiment, for a predetermined reference position (neutral position) of the focal position 52 is reflected essentially without a curvature effect from the mirror 34 and therefore essentially preserves its plane wavefront. For a displacement of the focal position 52 in the z direction from this neutral position, the control unit 38 may adjust the mirror 34 via the intermediary of the actuator arrangement 36 so that the plane wavefront of the incident laser beam 30 is converted into an essentially uniformly curved wavefront. Depending on the nature of the wavefront curvature, this may make the laser beam divergent or convergent. Such a change in the beam divergence leads to a displacement of the focal position 52 in the z direction, with expansion optics 32 otherwise arranged stationary and likewise with an unmoved focusing objective 50.

The control unit 38 controls the actuator arrangement 36 and therefore the deformation state of the mirror 34 in accordance with the cutting profile to be produced in the eye. A corresponding control program for the control unit 38 is stored in a memory (not shown in detail). The cutting profile, or the control program, specifies the way in which the focal point of the optical imaging system is to be displaced in the z direction for different positions in the x-y plane, and to this extent is representative of a focal point displacement profile in the sense of the invention. The precision and speed with which suitable actuators for the mirror 34 can be driven and actuated make it possible for z excursions of the beam focus in the range of a few tens of µm to be achieved within a few tens of ms or even a few ms. The focus of the f-theta objective 50 can therefore be adjusted within times which are required for effective and rapid lenticle cutting with an fs laser system. For example, a complete line scan with a beam focus z excursion of about 100 µm may readily be executed within a time of between about 10 ms and 40 ms, and under certain circumstances even less than 5 ms. The inventive use of adaptive, deformable mirrors in the beam path of the laser beam therefore achieves focus excursion frequencies such as are required for realistic application in femtosecond lenticle extraction.

In the variants according to FIGS. 3 and 4, components which are the same or have the same effect are provided with the same references as in FIG. 2 but with a lowercase letter added. In order to avoid unnecessary repetitions, reference is made to the previous explanations regarding FIG. 2 unless otherwise indicated below.

The exemplary embodiment of FIG. 3 also contains an adaptive mirror 34a in the beam path of the laser beam emerging from the laser source 28a. The adaptive mirror 34a, however, lies between the telescope 32a and the scanner 44a in the beam propagation direction. The expanded laser beam section 42a emerging from the telescope 32a accordingly has an essentially plane wavefront like the laser beam 30a on the entry side of the telescope 32a. Only the part of the laser beam—denoted by 62a—reflected by the mirror 34a and entering the scanner 44a has a curved wavefront according to the beam focus z position to be set, its degree of curvature depending on the desired z position of the beam focus.

Further passive deviating mirrors 64a, 66a are indicated in FIG. 3 for completeness, although they have no effect on the divergence of the laser beam.

The variant of the laser device according to FIG. 4 functions without a telescope for beam expansion of the laser beam. Instead, the adaptive mirror 34b itself is part of beam expansion optics, formed by a mirror combination which is composed of the adaptive mirror 34b and a further mirror 68b. The first mirror of this mirror combination to be encountered in the beam propagation direction of the laser beam 30b is a convex mirror, while the mirror encountered second is a concave mirror. In the exemplary case shown, the deformable mirror 34b constitutes the convex mirror, while the mirror 68b constitutes the concave mirror and is configured as a static mirror whose mirror surface is not adaptive. It is to be understood that in a modified embodiment, the concave mirror encountered second in the mirror combination may be configured adaptively while the mirror encountered first is static.

The mirror combination 34b, 68b causes beam expansion in a comparable way to a telescope. By suitable driving of the facets of the adaptive mirror 34b, it is possible to induce a divergence change of the laser beam which causes a corresponding displacement of the focal position 52b in the z direction, in a similar way as in the exemplary embodiments of FIGS. 2 and 3.

The exemplary embodiment of FIG. 4 is advantageous owing to its particularly simple beam guidance. It is furthermore possible for imaging errors possibly occurring (coma and astigmatism) to be compensated for by the deformable mirror 34b even in the neutral position. The term neutral position is intended to mean a reference state in which the focal position 52b assumes a defined z reference position. The use of reflective optics for the beam expansion, instead of transmissive optics, is advantageous particularly with wavelengths shorter than 400 nm for the lenticle cut.

In the exemplary embodiments described above, the adaptive mirror 34, 34a, 34b is preferably a DMD type (DMD: digital micromirror device) or an LCOS type (LCOS: liquid-crystal optical system) or a piezoelectrically controlled mirror. This, however, it is expressly not intended to exclude other working and actuation principles for the deformable mirror.

The invention claimed is:

1. A device for laser surgical ophthalmology, comprising:
a source of a pulsed femtosecond laser beam,
beam expansion optics in optical communication with the source of the pulsed femtosecond laser beam, the beam expansion optics configured to expand the pulsed femtosecond laser beam,
a scanner in optical communication with the beam expansion optics, the scanner configured to deflect the laser beam in a plane perpendicular to an axial beam path,
focusing optics in optical communication with the scanner, the focusing optics configured to focus the pulsed femtosecond laser beam,
a deformable mirror arranged between the source of the pulsed femtosecond laser beam and the focusing optics along the beam path, and
a program-controlled adjustment and control arrangement coupled to the deformable mirror, the program-controlled adjustment and control arrangement configured to deform the mirror for displacement of a focus of the pulsed femtosecond laser beam in the axial direction of the beam path in accordance with a predetermined cutting profile to be produced in a patient's eye.

2. The device of claim 1, wherein the focusing optics comprise an f-theta objective.

3. The device of claim 2, wherein the program-controlled adjustment and control arrangement includes at least one actuator for deforming the mirror.

4. The device of claim 3, wherein the at least one actuator is configured to adjust the focus of the pulsed femtosecond laser beam a distance of 100 μm in the axial direction in less than 40 ms.

5. The device of claim 4, wherein the at least one actuator is configured to adjust the focus of the pulsed femtosecond laser beam a distance of 100 μm in the axial direction in less than 5 ms.

6. The device of claim 3, wherein the deformable mirror is a digital micromirror device (DMD).

7. The device of claim 3, wherein the deformable mirror is a liquid-crystal optical system (LCOS).

* * * * *